(12) United States Patent
Asbaghi (10) Patent No.: US 6,884,237 B2
(45) Date of Patent: Apr. 26, 2005

(54) POSITION GUIDE FOR A NEEDLE GUARD (75) Inventor: Hooman A. Asbaghi, San Diego, CA (US)

(73) Assignee: Inviro Medical Devices, Inc., Vancouver (CA)

(*) Notice: Subject to any disclaimer, the term of this patent is extended or adjusted under 35 U.S.C. 154(b) by 109 days.

(21) Appl. No.: 10/316,610

(22) Filed: Dec. 10, 2002

(65) Prior Publication Data

US 2004/0111064 A1 Jun. 10, 2004

(51) Int. Cl.[7] .................................................. A61M 5/32
(52) U.S. Cl. ...................................... 604/198; 604/192
(58) Field of Search ................................ 604/110, 187, 604/192, 198, 263, 188, 171, 197, 111, 207

(56) References Cited

U.S. PATENT DOCUMENTS

| 4,813,940 | A | * | 3/1989 | Parry .......................... 604/198 |
| 4,894,055 | A | | 1/1990 | Sudnak |
| 4,911,693 | A | | 3/1990 | Paris |
| 5,242,401 | A | | 9/1993 | Colsky |
| 5,267,977 | A | | 12/1993 | Feeney, Jr. |
| 5,292,314 | A | | 3/1994 | D'Alessio et al. |
| 5,295,975 | A | | 3/1994 | Lockwood, Jr. |
| 5,300,040 | A | * | 4/1994 | Martin ........................ 604/198 |
| 5,389,085 | A | | 2/1995 | D'Alessio et al. |
| 5,478,316 | A | | 12/1995 | Bitdinger et al. |
| 5,591,138 | A | * | 1/1997 | Vaillancourt ................. 604/263 |
| 5,688,241 | A | | 11/1997 | Asbaghi |
| 5,795,336 | A | * | 8/1998 | Romano et al. ............. 604/192 |
| 6,162,197 | A | * | 12/2000 | Mohammad ................. 604/195 |
| 6,379,336 | B1 | | 4/2002 | Asbaghi et al. |
| 6,547,764 | B1 | * | 4/2003 | Larsen et al. ................ 604/192 |

* cited by examiner

Primary Examiner—Manuel Mendez
(74) Attorney, Agent, or Firm—Nydegger & Associates (57) ABSTRACT A device for covering and protecting a syringe needle after a syringe procedure includes a needle guard component, a base member component and a spring. The needle guard and base member components of the device are both formed with cylindrical shaped portions that are arranged coaxially. The base member is affixable to the syringe with the spring positioned between the needle guard and base member components to urge the components in opposite axial directions. One component is formed with a plug that extends into a guide mechanism formed on the other component. The guide mechanism includes a locking cutout, an axially aligned linear track and a deflectable arm. The arm deflects to allow linear plug movement during retraction of the needle guard over the needle and redirects the plug to the locking cutout when the needle guard moves to re-cover the needle.

20 Claims, 4 Drawing Sheets

POSITION GUIDE FOR A NEEDLE GUARD

FIELD OF THE INVENTION

The present invention pertains generally to syringes for medical use. More particularly, the present invention pertains to passive safety devices for medical syringes. The present invention is particularly, but not exclusively, useful for passively covering and protecting the needle of a medical syringe at the completion of a syringe procedure.

BACKGROUND OF THE INVENTION

Accidental needle sticks can occur in several ways. For example, a sudden movement by a patient can cause a health care worker to lose control of a syringe, resulting in injury. Additionally, injuries often result when contaminated, unprotected needles are left unattended or are disposed of improperly. Moreover, attempts to manually recap a needle after filling the syringe with a medicament or attempts to recap a syringe needle following a syringe procedure can also result in injury. In addition to accidental needle sticks, unnecessary exposure to bloodborne pathogens can result when a health care worker mistakenly re-uses a contaminated needle on a patient.

Unfortunately, accidental needle sticks have the potential to expose a health care worker to a life-threatening virus such as hepatitis or HIV. For each accidental needle stick, health care providers are obligated to test and counsel the exposed worker. Further, follow-up testing for HIV must be conducted approximately six months after the exposure. It is to be appreciated that the costs associated with the testing, lab work, the workers lost time, and the associated tracking and administrative costs, can be considerable.

Heretofore, passive needle protection systems have been disclosed having needle guards that are designed to contact a patient's skin during a syringe procedure. In many of these devices, this contact establishes a relative movement between the needle guard and syringe when the needle is inserted into and withdrawn from the patient. The relative movement can then be used to move the needle guard (relative to the syringe) from an initial position to an intermediate position during needle insertion and from the intermediate position to a final position during needle withdrawal. In these systems, the final needle guard position generally corresponds to a needle guard position in which the needle guard both covers the needle and is locked in place.

One way to place the needle guard into such an intermediate position is to provide a mechanism to rotate the needle guard relative to the needle during needle insertion (i.e. rotation during needle guard movement from the initial position to the intermediate position). However, this rotation is restrained by the frictional force between the needle guard arid the skin. Generally, this restraint prevents the relatively smooth action required to accurately insert the needle into a target location such as a vein. In some cases, the inability of the needle guard to rotate smoothly can prevent the needle guard from properly retracting. When this happens, the needle cannot be inserted to the proper penetration depth and the result is often an unsuccessful syringe procedure.

In light of the above, it is an object of the present invention to provide a protective device that is installable on a medical syringe and is capable of passively covering and protecting the needle of the syringe after the syringe has been used to perform a syringe procedure on a patient. It is another object of the present invention to provide a protective device having a needle guard that does not rotate relative to the syringe needle during insertion of the needle into the patient. Yet another object of the present invention is to provide a protective device for a medical syringe that is reliable and easy to use.

SUMMARY OF THE INVENTION

A device for covering and protecting the hollow needle of a syringe, after the syringe has been used to perform a syringe procedure on a patient includes a needle guard component, a base member component and a coil spring. The device can be used for syringe procedures that include but are not necessarily limited to an injection using a fillable, prefilled or cartridge loaded syringe, and an aspiration procedure to include a blood collection procedure.

In functional overview, the device is installed on the syringe prior to a syringe procedure. During the syringe procedure, the needle guard of the device retracts over the needle allowing the needle to be inserted into the patient. Upon withdrawal of the needle from the patient, the device passively re-covers the needle, locking the needle guard over the tip of the needle to prevent accidental needle sticks or inadvertent re-use of the syringe.

In greater structural detail, the needle guard and base member components of the device are each formed with a cylindrical shaped portion sized to allow the cylindrical portion of one component to slide over the cylindrical shaped portion of the other component. With this cooperation of structure, the cylindrical portions can be coaxially positioned on a single axis to allow for the reciprocal axial movement of the needle guard relative to the base member. Also, an aperture extends through the needle guard/base member assembly that is sized to allow the needle of the syringe to pass through the aperture. This cooperation of structure allows the spring to be seated between the needle guard and the base member to urge the needle guard and base member in opposite axial directions.

For the present invention, the base member is affixable to the syringe and when so affixed moves with the syringe and its needle. On the other hand, the needle guard is axially moveable relative to the base member and needle, and these movements are controlled by the cooperative interaction between a plug and guide mechanism. In greater detail, one of the device components (i.e. either the needle guard or the base member) is formed with a plug that extends from the cylindrical portion of the component and the other component is formed with a guide mechanism. More specifically, the cylindrical portion of one component is formed with a guide mechanism that includes a locking cutout, an axially aligned linear track and a deflectable arm.

The deflectable arm extends into the linear track and is oriented to be deflected out of the linear track by the plug during movement of the needle guard in a proximal direction relative to the base member. This deflection allows the plug to pass the arm during travel within the linear track when the needle guard is retracting over the needle. Further, since the plug travels within the linear track, the needle guard retracts over the needle without rotation relative to the needle. On the other hand, when the needle guard moves back to cover the needle (i.e. during needle withdrawal when the needle guard moves distally relative to the needle) a different interaction between the plug and arm occurs. Specifically, the arm does not deflect but instead remains in the linear track and directs the plug from the linear track to the locking cutout. To maintain the plug in the locking cutout, one of the device components (i.e. either the base member or the needle guard) is formed with a tab and the other is formed with a slot. The slot and tab are positioned on the components to allow the slot to interact with the tab when the plug is located in the locking cutout to prevent rotation of the needle guard relative to the base member.

In operation, the base member of the device is affixed to the syringe and the device is initially configured with the plug located at a first position that is at or near a first end of the linear track. With the plug at the first position, a small portion of needle typically, but not necessarily, extends distally from the needle guard and thus is exposed to allow the needle tip to be accurately located on the patient to initiate the syringe procedure. Next, the needle tip is pushed into the body of the patient until the needle guard contacts the patient. Upon contact between the needle guard and the patient, movement of the needle guard stops. Meanwhile, the syringe and base member can be further translated towards the patient, inserting the needle to the proper penetration depth. As the base member and needle move relative to the needle guard, the plug is directed along the linear track and past the deflecting arm (as described above) to a second position that is at or near the second end of the linear track. If desired, the second end of the linear track can be positioned to limit the maximum needle penetration depth.

With the needle inserted into the patient at a desired penetration depth, the syringe can be used to inject or withdraw fluid from the patient. Next, the needle is removed from the patient. During the initial withdrawal of the needle from the patient, the needle guard remains in contact with the patient while the syringe and base member are pulled away from the patient. Specifically, the spring expands to hold the needle guard against the patient during initial withdrawal. In addition, the movement of the base member relative to the needle guard during needle removal causes the plug to translate along the linear track from the second position and towards the arm. At the arm, the plug is directed from the linear track and to the locking cutout that is located at a position to ensure that the needle guard covers the needle when the plug is in the locking cutout. As indicated above, an interaction between a slot and tab prevents the plug from rotating out of the locking cutout. Thus, once the plug is in the locking cutout, the needle guard becomes locked over the needle to protect against accidental needle sticks or inadvertent re-use.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
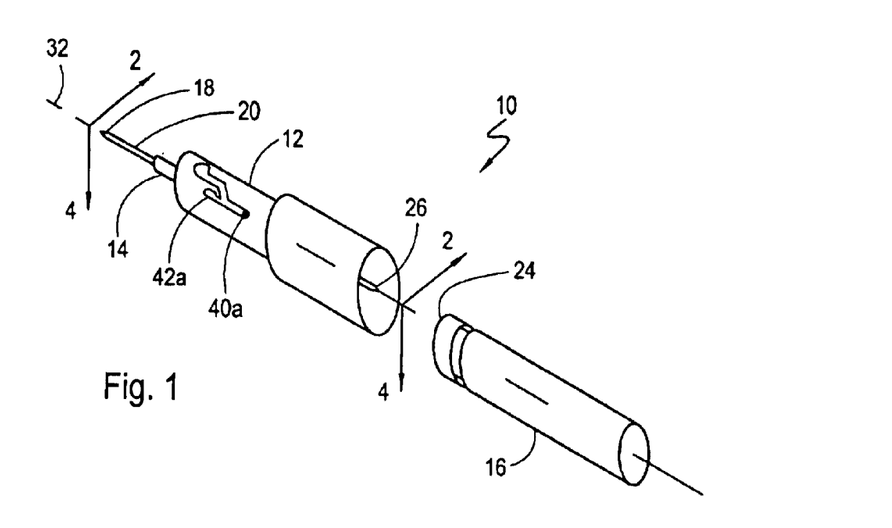
FIG. 1 is an exploded perspective view of a blood collection system having a mechanism to passively cover and protect the needle at the completion of a blood collection procedure.

Referring initially to FIG. 1, a blood collection system is shown and generally designated 10. As shown, the system 10 includes a base member 12 and a needle guard 14. Functionally, the system 10 can be used to safely draw blood from a patient and into the blood collection vial 16. Specifically, the distal tip 18 of the hollow needle 20 can be used to pierce a patient's vein causing blood to flow into the hollow needle 20. As further shown, a septum 24 can be placed over the opening of the blood collection vial 16 allowing the septum 24 to be pierced by the proximal tip 26 of the needle 20 to establish fluid communication between the blood collection vial 16 and the needle 20.

In functional overview, the interaction between the base member 12 and the needle guard 14 causes the needle guard 14 to retract over the needle 20 during insertion of the needle 20 into a patient. After the needle 20 has been withdrawn from the patient, the needle guard 14 passively re-covers and is locked in place over the distal tip 18 of the needle 20 to prevent accidental needle sticks or inadvertent re-use of the system 10.

Figure 2:
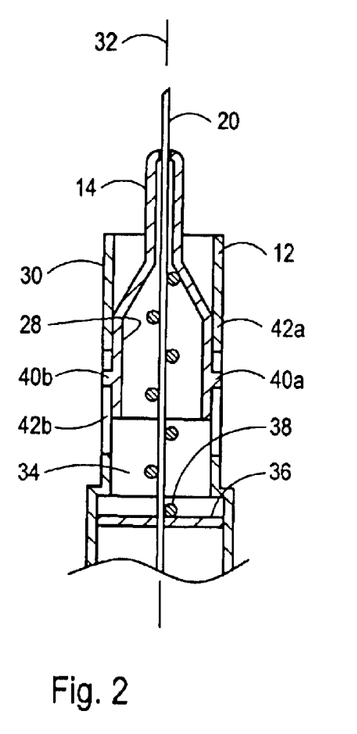
FIG. 2 is a cross sectional view of the distal portion of the blood collection system shown in FIG. 1 as seen along the line 2—2 in FIG. 1.

A better appreciation of the interaction between the base member 12 and the needle guard 14 can be obtained with cross-reference to FIGS. 1 and 2. As shown, the needle guard 14 is formed with a cylindrical shaped portion 28. Also shown, the base member 12 is formed with a cylindrical shaped portion 30 that is sized to slide over the cylindrical shaped portion 28 of the needle guard 14. It can be further seen in FIG. 2 that the cylindrical portions 28, 30 are coaxially positioned on axis 32 to allow for the reciprocal axial movement of the needle guard 14 relative to the base member 12. Also, the needle guard 14 and base member 12 are shaped to establish a continuous aperture 34 that extends through both the needle guard 14 and base member 12 with the aperture 34 being sized to allow the needle 20 to pass through the aperture 34.

With continued cross-reference to FIGS. 1 and 2, it can be seen that the syringe for the blood collection system 10 includes the needle 20, the blood collection vial 16 and a retainer 36 that is provided to hold the needle 20. As best seen in FIG. 2, the base member 12 is affixed to the retainer 36 and accordingly, the base member 12 moves together with the retainer 36 and the needle 20. Also shown in FIG.

2, a coil spring 38 is seated between the needle guard 14 and retainer 36 to urge the needle guard 14 and base member 12 in opposite axial directions.

For the system 10, movements of the needle guard 14 relative to the base member 12 are controlled by the cooperative interaction between a pair of plugs 40a,b and a pair of guide mechanisms 42a,b. In greater detail, the base member 12 is formed with a pair of identical, diametrically opposed guide mechanisms 42a,b that are each formed in the cylindrical portion 30 of the base member 12. As further seen in FIG. 2, the needle guard 14 is formed with a pair of diametrically opposed plugs 40a,b that each extend radially outwardly from the cylindrical portion 28 of the needle guard 14 and into a respective guide mechanism 42a,b. Although a pair of diametrically opposed plug/guide mechanisms are shown, it is to be appreciated that a single plug/guide mechanism could be used to control the movement of the needle guard 14 relative to the base member 12.

Figure 3A:
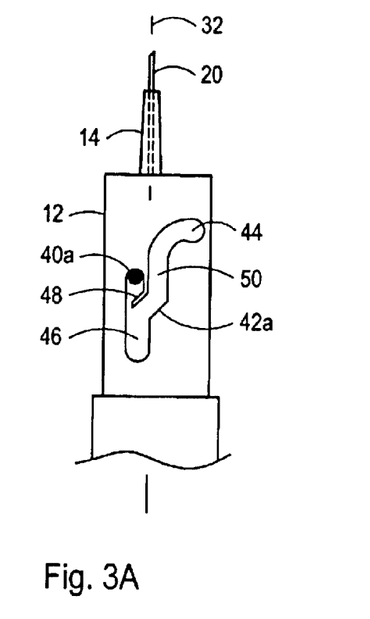
FIGS. 3A–3E are a series of front elevation views of the blood collection system shown in FIG. 1 showing the sequence of plug positions that occur during a blood collection procedure.
Figure 3B:
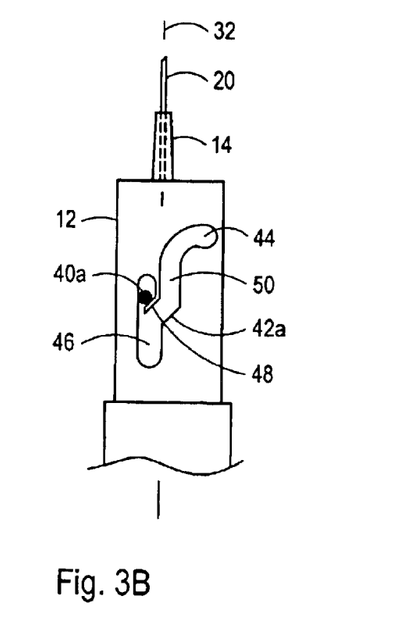

With cross-reference now to FIGS. 2 and 3A, it can be seen that each guide mechanism 42a,b includes a locking cutout 44, an axially aligned linear track 46, a deflectable arm 48 and an axially aligned linear track 50. As best seen with cross reference to FIGS. 3A and 3B, the deflectable arm 48 extends into the linear track 46 and is oriented to be deflected out of the linear track 46 by the plug 40a (see FIG. 3B) during movement of the needle guard 14 in a proximal direction relative to the base member 12. This deflection allows the plug 40a to pass the arm 48 during travel within the linear track 46 from a first position (shown in FIG. 3a) to a second position (shown in FIG. 3C). This movement of the plug 40a from the first position (shown in FIG. 3a) to the second position (shown in FIG. 3C) corresponds to a proximal movement of the needle guard 14 relative to the base member 12 and typically occurs when the needle 20 is inserted into a patient. It is to be appreciated that since the plug 40a travels within the linear track 46, the needle guard 14 retracts over the needle 20 without substantial rotation relative to the needle 20 or base member 12.

Figure 3C:
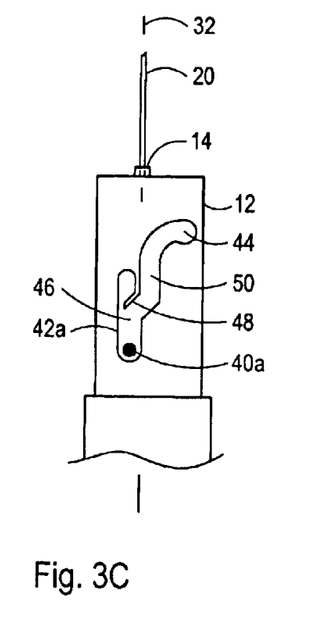
Figure 3D:
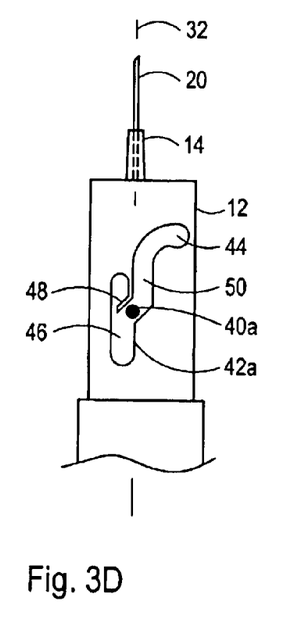
Figure 3E:
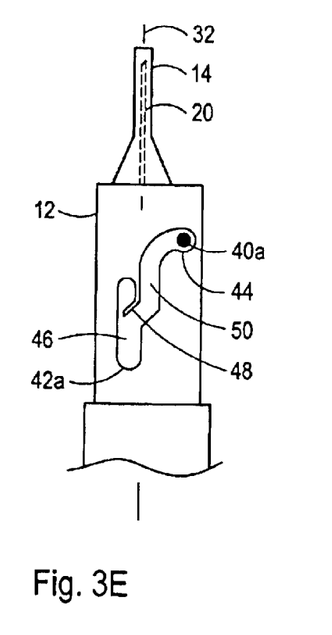

With cross-reference now to FIGS. 3C, 3D and 3E, it can be seen that as the needle guard 14 moves back to cover the needle 20 (i.e. from the position shown in FIG. 3C to the position shown in FIG. 3E), the arm 48 directs the plug 40a (See FIG. 3D) from the linear track 46 to the locking cutout 44. In the embodiment shown, an axially aligned linear track 50 is provided between the arm 48 and the locking cutout 44. The linear track 50 allows the needle 20 to be partially exposed initially (as shown in FIG. 3A) and fully covered when the plug 40a is in the locking cutout 44. It is to be appreciated that in implementations of the system 10 where it is desired to fully cover the needle 20 initially, the plug 40a may be directed directly into a locking cutout 44 without a linear track 50.

Figure 4:
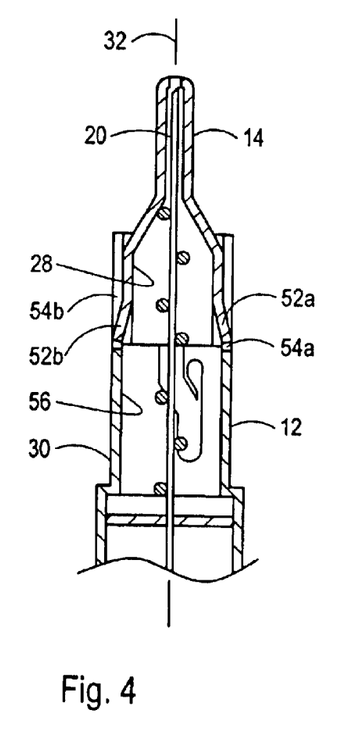
FIG. 4 is a cross sectional view of the distal portion of the blood collection system shown in FIG. 1 as seen along the line 4—4 in FIG. 1 showing a pair of tabs that interact with a pair of slots to prevent rotation of the needle guard relative to the base member when the plug is in the locking cutout.

Referring now to FIG. 4, it can be seen that the needle guard 14 is formed with a pair of diametrically opposed tabs 52a,b. For the system 10, each tab 52a,b, in the relaxed state, extends outwardly from the cylindrical portion 28 of the needle guard 14. Also shown in FIG. 4, the base member 12 is formed with a pair of diametrically opposed slots 54a,b positioned for interaction with the respective tabs 52a,b when the plug 40a is located in the locking cutout 44 (see FIG. 3E). The tabs 52a,b and slots 54a,b are provided to prevent rotation of the needle guard 14 relative to the base member 12 when the plug 40a is in the locking cutout 44. In greater detail, when the plug 40a is in either of the linear tracks 46, 50, the tabs 52a,b are misaligned with the respective slots 54a,b. During this misalignment, the tabs 52a,b are biased inwardly toward the axis 32 and ride along the inner surface 56 of the cylindrical portion 30 of the base member 12. However, when the plug 40a is directed into the locking cutout 44, the needle guard 14 rotates relative to the base member 12, and this rotation aligns each tab 52a,b with a respective slot 54a,b. When aligned, each tab 52a,b springs into a respective slot 54a,b to prohibit further rotation of the needle guard 14 relative to the base member 12.

The operation of the system 10 can best be appreciated with initial reference to FIGS. 1 and 3A. In preparation for use, the septum 24 of the blood collection vial 16 is pierced by the proximal tip 26 of the needle 20 to establish fluid communication between the distal tip 18 of the needle 20 and the blood collection vial 16. Also in preparation for use, the plug 40a is located at a first position (shown in FIG. 3A) that is at or near a first end of the linear track 46. With the plug 40a at the first position, a small portion of the needle 20 extends distally from the needle guard 14 and is thus exposed to allow the distal tip 18 of the needle 20 to be accurately located on the patient to initiate the syringe procedure. Next, the distal tip 18 of the needle 20 is pushed into the body of the patient until the needle guard 14 contacts the patient. Upon contact between the needle guard 14 and the patient, movement of the needle guard 14 stops. Meanwhile, the needle 20 and base member 12 can be further translated towards the patient, inserting the needle 20 into a pre-selected vein of the patient. As the base member 12 and needle 20 move relative to the needle guard 14, the plug 40a is directed along the linear track 46, past the deflecting arm 48 to a second position in the linear track 46 that is at or near the second end of the linear track 46 (second position shown in FIG. 3C). If desired, the second end of the linear track 46 can be positioned to limit the maximum needle penetration depth.

With the needle 20 inserted into a pre-selected vein of the patient at a desired penetration depth, the system 10 can be used to draw blood from the patient. Once a desired amount of blood has been collected, the needle 20 is removed from the patient. During the initial withdrawal of the needle 20 from the patient, the needle guard 14 remains in contact with the patient while the base member 12 is pulled away from the patient. Specifically, the spring 38 (see FIG. 2) expands to hold the needle guard 14 against the patient during initial withdrawal. In addition, the movement of the base member 12 relative to the needle guard 14 during needle removal causes the plug 40a to translate along the linear track 46 from the second position (shown in FIG. 3C) and towards the arm 48. At the arm 48, the plug 40a is directed from the linear track 46 and to the linear track 50. The continued expansion of the spring 38 drives the needle guard 14 distally relative to the base member 12 until the plug 40a reaches the locking cutout 44 (plug 40a shown positioned in locking cutout 44 in FIG. 3E). As shown in FIG. 3E, the locking cutout 44 is positioned on the base member 12 at a location wherein the needle guard 14 completely covers the needle 20 when the plug 40a is in the locking cutout 44. Once the plug 40a is in the locking cutout 44, the interaction between the slots 54a,b and tabs 52a,b (See FIG. 4) prevent the plug 40a from rotating out of the locking cutout 44. As such, once the plug 40a is in the locking cutout 44, the needle guard 14 becomes locked over the needle 20 to protect against accidental needle sticks or inadvertent re-use.

Figure 5:
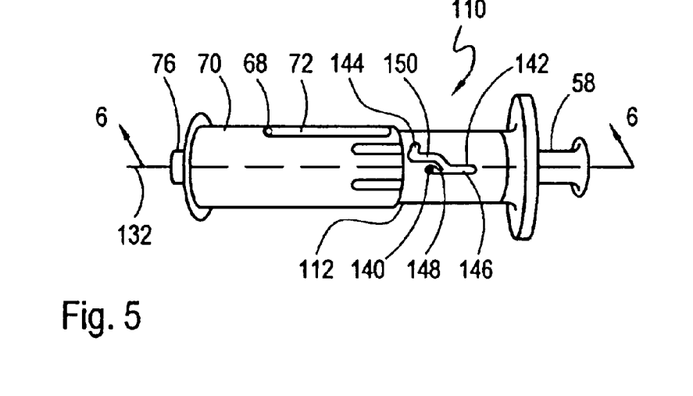
FIG. 5 is a perspective view of a prefilled injection syringe system having a mechanism to passively cover and protect the needle at the completion of an injection procedure.
Figure 6:
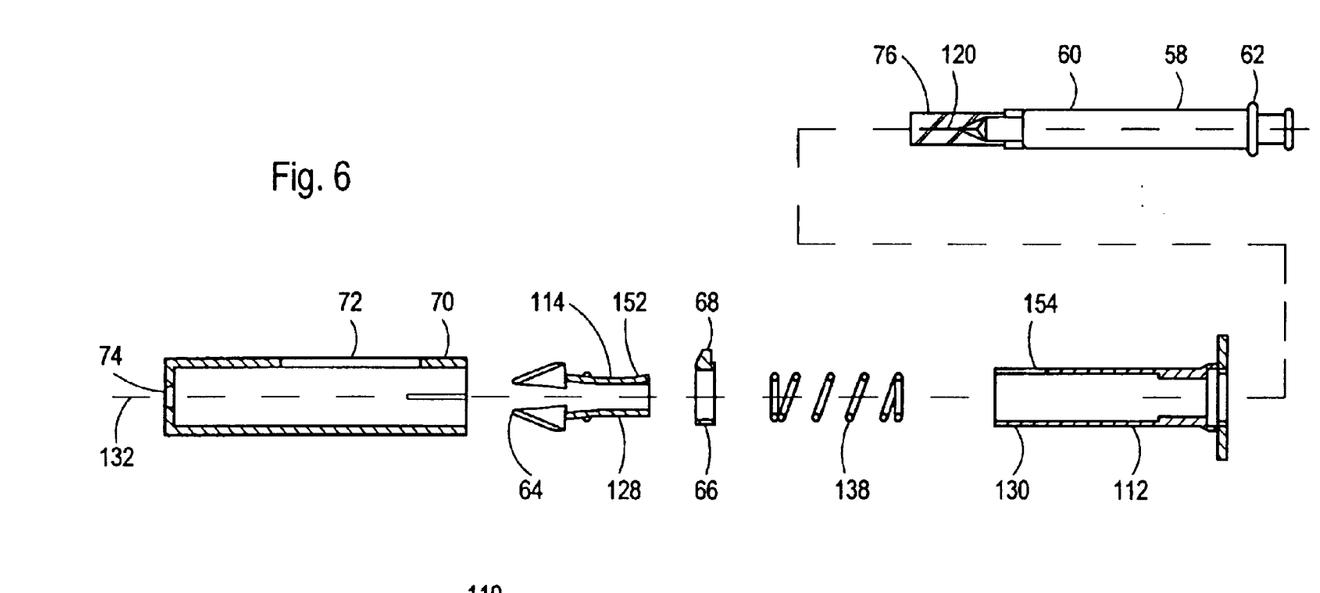
FIG. 6 is an exploded, sectional view of the prefilled injection syringe system shown in FIG. 5 as seen along line 6—6 in FIG. 5.

Referring now with cross-reference to FIGS. 5 and 6, a system 110 for safely performing an injection includes a sheathed, prefilled injection syringe 58. As further shown, the system 110 includes a needle guard 114, a base member 112 and a coil spring 138. Also shown, the base member 112 is formed with a cylindrical portion 130 that is large enough to slide over the barrel 60 of the syringe 58 allowing attachment of the proximal end of the base member 112 to the finger guard 62 of the syringe 58. Like the base member 112, the needle guard 114 is formed with a cylindrical portion 128 and the cylindrical portions 128, 130 are co-axially positioned on axis 132. As further shown, the cylindrical portion 128 of the needle guard 114 is sized for insertion into the cylindrical portion 130 of the base member 112. With this combination of structure, the base member 112 is disposed over the needle guard 114 allowing both axial and rotational movement between the needle guard 114 and base member 112. FIG. 6 further shows that spring 138 is mounted between the needle guard 114 and the base member 112 to urge the needle guard 114 in a distal direction relative to the base member 112.

Figure 7:
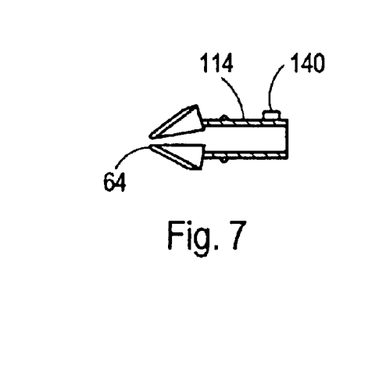
FIG. 7 is a sectional view of the needle guard as in FIG. 6, but shown in the contracted state and rotated 90 degrees about the axis shown in FIG. 6 to show the plug of the guard.

With cross-reference now to FIGS. 5, 6 and 7, it can be seen that the relative movement between the needle guard 114 and the base member 112 during an injection is controlled using a plug 140 formed on the needle guard 114 that interacts with a guide mechanism 142 formed in the base member 112. As shown, the guide mechanism 142 includes a locking cutout 144, an axially aligned linear track 146, a deflectable arm 148 and an axially aligned linear track 150. The deflectable arm 148 extends into the linear track 146 and is oriented to be deflected out of the linear track 146 by the plug 140 during movement of the needle guard 114 in a proximal direction relative to the base member 112. This deflection allows the plug 140 to pass the arm 148 during travel within the linear track 146 corresponding to a proximal movement of needle guard 114 relative to the base member 112 and typically occurs when the needle 120 is inserted into a patient. It is to be appreciated that since the plug 140 travels within the linear track 146, the needle guard 114 retracts over the needle 120 without substantial rotation relative to the needle 120. It can be further seen that as the needle guard 114 moves back to cover the needle 120, the arm 148 directs the plug 140 from the linear track 146 to the linear track 150 and then to the locking cutout 144.

Referring now to FIG. 6, it can be seen that the needle guard 114 is formed with a tab 152, that in the relaxed state, extends outwardly from the cylindrical portion 128 of the needle guard 114. Also shown in FIG. 6, the base member 112 is formed with a slot 154 positioned for interaction with the tab 152 when the plug 140 is located in the locking cutout 144. When the plug 140 is in either of the linear tracks 146, 150, the tab 152 is misaligned with the slot 154. During this misalignment, the tab 152 is biased inwardly toward the axis 132 and rides along the inner surface of the cylindrical portion 130 of the base member 112. However, when the plug 140 is directed into the locking cutout 144, the needle guard 114 rotates relative to the base member 112, and this rotation aligns tab 152 with slot 154. When aligned, tab 152 springs into slot 154 to prohibit further rotation of the needle guard 114 relative to the base member 112.

With cross-reference now to FIGS. 5 and 6, it can be seen that the needle guard 114 extends to a distal tip 64 that is formed with a dilatable opening. Functionally, the distal portion of the needle guard 114 is reconfigurable between a first configuration in which the opening is relatively large (shown in FIG. 6) and a second configuration in which the opening is relatively small (shown in FIG. 7). With the distal portion of the needle guard 114 in the first configuration, the relatively large opening allows the sheathed needle 120 of the injection syringe 58 to pass through the end of the needle guard 114 during attachment of the base member 112/needle guard 114 assembly to the syringe 58. On the other hand, in the second configuration, the relatively small opening allows for syringe injections at relatively large angles from the normal at the injection site. To reconfigure the needle guard 114 and contract the opening, the system 110 further includes a moveable ring 66 that is positioned over the distal portion of the needle guard 114. To facilitate movement of the ring 66 over the needle guard 114, the ring 66 is formed with a lug 68 that extends from the ring 66. As further shown, the system 110 includes a cover 70 for interaction with the lug 68. In operation, an axially aligned slot 72 formed in the cover 70 allows the cover 70 to engage the lug 68 and thereby move the lug 68 and ring 66 distally as the cover 70 is withdrawn from the injection syringe 58.

Continuing now with reference to FIG. 6, the cover 70 is formed with an aperture 74 for receiving and holding the sheath 76 of the prefilled injection syringe 58. This allows the resilient sheath 76 to pass into the aperture 74 and become affixed to the cover 70 when the cover 70 is installed onto the sheathed, prefilled injection syringe 58. With the sheath 76 attached to the cover 70, the sheath 76 can be safely removed from the prefilled injection syringe 58 when the cover 70 is withdrawn from the needle guard 114. A more detailed description of the interactive cooperation between the needle guard 114, ring 66 and cover 70 is disclosed in co-pending patent application Ser. No. 10/032,342, entitled Safety Device For a Sheathed, Prefilled Injection Syringe to Hooman A. Asbaghi, filed on Dec. 21, 2001, the contents of which are hereby incorporated by reference herein.

Figure 8:
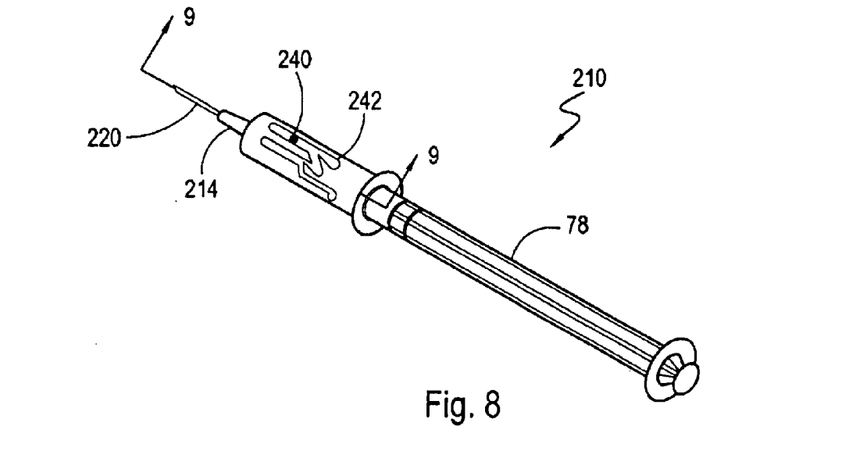
FIG. 8 is a perspective view of a fillable injection syringe system having a mechanism to passively cover and protect the needle at the completion of an injection procedure.
Figure 9:
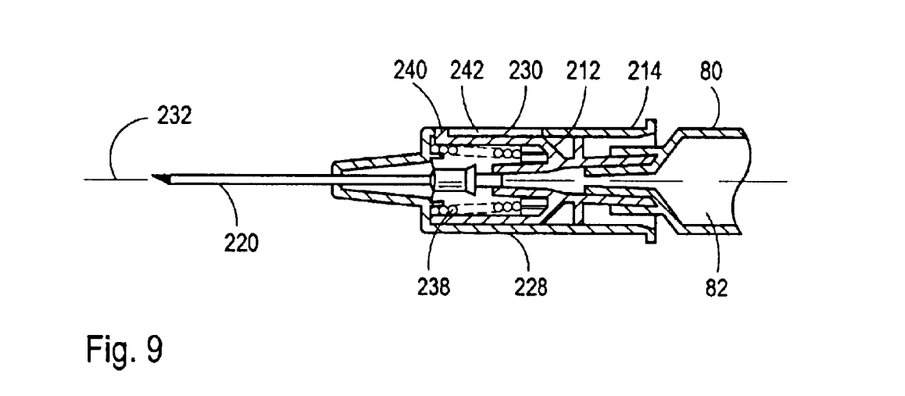
FIG. 9 is a sectional view of a distal portion of the system shown in FIG. 8.

Referring now with cross-reference to FIGS. 8 and 9, a system 210 for safely performing an injection includes a fillable injection syringe 78. As further shown, the system 210 includes a needle guard 214, a base member 212 and a coil spring 238. Also shown, the base member 212 is attached to both the hollow needle 220 and the body 80 of the syringe 78. As shown, this attachment places the lumen of the hollow needle 220 in fluid communication with the medicament chamber 82. A more detailed description of the interaction between the base member 212, needle 220 and syringe body 80 is disclosed in co-pending patent application Ser. No. 09/843,282 entitled Protective Device For a Fillable Injection Syringe, to Hooman A. Asbaghi, filed on Apr. 25, 2001, the contents of which are hereby incorporated by reference herein.

Continuing with cross-reference to FIGS. 8 and 9, it can be seen that the base member 212 is formed with a cylindrical portion 230, the needle guard 214 is formed with a cylindrical portion 228 and the cylindrical portions 228, 230 are co-axially positioned on axis 232. As further shown, the cylindrical portion 230 of the base member 212 is sized for insertion into the cylindrical portion 228 of the needle guard 214. With this combination of structure, the needle guard 214 is disposed over the base member 212 allowing both axial and rotational movement between the needle guard 214 and base member 212. Spring 238 is mounted between the needle guard 214 and the base member 212 to urge the needle guard 214 in a distal direction, relative to the base member 212.

Figure 10:
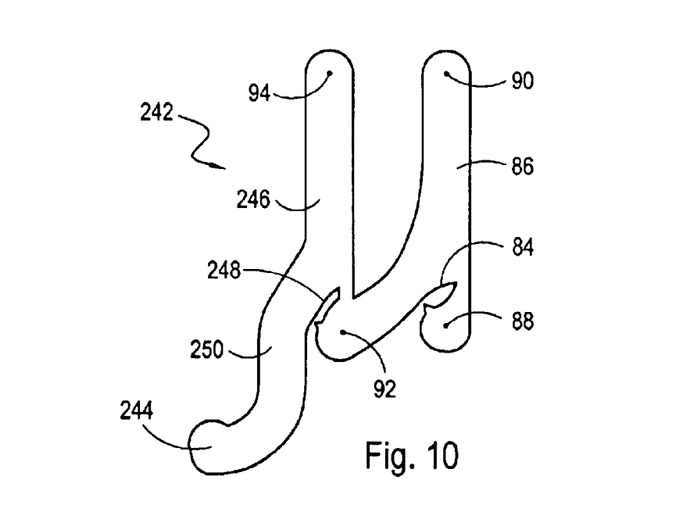
FIG. 10 is an enlarged view of the guide mechanism for the system shown in FIG. 8.

With cross-reference now to FIGS. 8, 9 and 10, it can be seen that relative movement between the needle guard 214 and the base member 212 during an injection is controlled using a plug 240 formed on the base member 212 that interacts with a guide mechanism 242 formed in the needle guard 214. As best seen in FIG. 10, the guide mechanism 242 includes a locking cutout 244, an axially aligned linear track 246, a deflectable arm 248, an axially aligned linear track 250, a deflectable arm 84 and an axially aligned linear track 86. As shown, the deflectable arms 84 and 248 extend into respective linear tracks 86 and 246 and are oriented to be deflected out of the respective linear tracks 86 and 246 by the plug 240 during movement of the needle guard 214 in a proximal direction relative to the base member 212. This deflection allows the plug 240 to pass the arms 84 and 248 when traveling within respective linear tracks 86 and 246 during proximal movement of needle guard 214 relative to the base member 212.

In operation, the plug 240 is initially located at position 88 which is typically sited on the needle guard 214 to cause a relatively short portion of the hollow needle 220 to extend distally from the needle guard 214. Then, to fill the syringe 78 with a fluid medicament, the needle 220 is inserted through the stopple of a medicine vial (not shown). In response, the medicine vial pushes against the needle guard 214 causing the needle guard 214 to move in a proximal direction back over the base member 212. This also moves the plug 240 from position 88, past the arm 84 to position 90. When the needle 220 is disengaged from the medicine vial, the spring 238 urges the needle guard 214 forward in a distal direction. This also moves the plug 240 from position 90 and toward the arm 84. At the arm 84, the plug 240 is deflected into position 92. Typically, position 92 is sited on the needle guard 214 to cause a relatively short portion of the needle 220 to again extend distally from the needle guard 214. The syringe 78 is now filled with medicament and ready for injecting the fluid medicament into the patient.

To inject the medicament into the patient, the distal tip of the needle 220 is pushed into the body of the patient until the needle guard 214 contacts the patient. Upon contact between the needle guard 214 and the patient, movement of the needle guard 214 stops. Meanwhile, the needle 220 and base member 212 can be further translated towards the patient, inserting the needle 220 into the patient. As the base member 212 and needle 220 move relative to the needle guard 214, the plug 240 is directed along the linear track 246 from position 92, past the deflecting arm 248, and into position 94. If desired, position 94 can be sited on the needle guard 214 to limit the maximum needle penetration depth.

With the needle 220 inserted into the patient at a desired penetration depth, the system 210 can be used to inject the medicament into the patient. Once a desired amount of medicament has been injected, the needle 220 is removed from the patient. During the initial withdrawal of the needle 220 from the patient, the needle guard 214 remains in contact with the patient while the base member 212 is pulled away from the patient. Specifically, the spring 238 expands to hold the needle guard 214 against the patient during initial withdrawal. In addition, the movement of the base member 212 relative to the needle guard 214 during needle removal causes the plug 240 to translate along the linear track 246 from position 94 and towards the arm 248. At the arm 248, the plug 240 is directed from the linear track 246 and to the linear track 250. The continued expansion of the spring 238 drives the needle guard 214 distally relative to the base member 212 until the plug 240 reaches the locking cutout 244. For the system 210, the locking cutout 244 is sited on the needle guard 214 at a location wherein the needle guard 214 completely covers the needle 220 when the plug 240 is in the locking cutout 244.

While the particular devices, systems and methods as herein shown and disclosed in detail are fully capable of obtaining the objects and providing the advantages herein before stated, it is to be understood that they are merely illustrative of the presently preferred embodiments of the invention and that no limitations are intended to the details of construction or design herein shown other than as described in the appended claims.

What is claimed is:

1. A device for protecting the needle of a syringe, said device comprising:

a cylindrical base member affixable to the syringe;

a hollow cylindrical needle guard defining an axis, said needle guard positioned coaxially with said base member for reciprocal axial movement relative thereto with one of said base member and said needle guard formed with a plug and the other formed with a guide means for interaction with said plug, said guide means having a locking cutout, a linear track substantially aligned with said axis and a deflectable arm positioned in said linear track and aligned to allow said plug to travel within said linear track and past said arm during proximal movement of said needle guard relative to the needle and thereafter direct said plug into said locking cutout during distal advancement of said needle guard relative to the needle; and a biasing means disposed between said needle guard and said base member to urge said needle guard and said base member in opposite axial directions and, in sequence, to hold said plug at a first initial position in said linear track and then allow said plug to travel within said linear track and past said arm in response to an external axially directed force retracting said needle guard over the needle without relative rotation therebetween and to subsequently move said plug into said arm for deflection into said locking cut out to cover and protect the needle with said needle guard upon removal of the axially directed external force.

2. A device as recited in claim 1 wherein said biasing means is a spring.

3. A device as recited in claim 1 wherein a first length of said needle extends from said guard when said plug is held in said first position in said linear track.

4. A device as recited in claim 1 wherein said linear track is a first linear track and said guiding means is formed with a second linear track aligned substantially parallel to said axis and formed with a distal end, and wherein said locking cutout is positioned at said distal end of said second linear track, said arm being positioned to deflect said plug from said first linear track to said second linear track and into said locking cutout during distal advancement of said needle guard relative to the needle.

5. A device as recited in claim 1 wherein said base member is formed with said guide means and said needle guard is formed with said plug.

6. A device as recited in claim 5 wherein said plug extends radially from said needle guard.

7. A device as recited in claim 6 wherein a portion of said cylindrical needle guard is positioned in said cylindrical base member.

8. A device as recited in claim 7 wherein said needle guard is formed with a tab and said base member is formed with a slot for interaction with said tab when said plug is located in said locking cutout to prevent rotation of said needle guard relative to said base member.

9. A device as recited in claim 1 wherein one of said base member and said needle guard is formed with a tab and the other is formed with a slot for interaction with said tab when said plug is located in said locking cutout to prevent rotation of said needle guard relative to said base member.

10. A device for protecting a syringe needle after the syringe has been used on a patient, said device comprising:

an elongated needle guard defining an axis, said guard formed with an aperture for receiving the needle therethrough;

a base member affixable to the syringe;

a means for biasing said needle guard along said axis in a distal direction from said base member; and a means for interconnecting said needle guard with said base member to initially hold said needle guard in a first axial position relative to said base member in response to said biasing means, and for sequentially directing said guard into a second axial position relative to said base member without relative rotation between said needle guard and said base member and thereafter directing said needle guard into a needle-protecting third position relative to said base member in response to a selectively applied axial force against said needle guard in opposition to said biasing means.

11. A device as recited in claim 10 wherein said biasing means is a coil spring.

12. A device as recited in claim 10 wherein said interconnecting means comprises:

a plug formed on said needle guard and extending therefrom; and a guide means formed in said base member for interaction with said plug, said guide means having a locking cutout, a linear track substantially aligned with said axis and a deflectable arm positioned in said linear track and aligned to allow said plug to travel within said linear track and past said arm during proximal movement of said needle guard relative to the needle and thereafter direct said plug into said locking cutout during distal advancement of said needle guard relative to the needle.

13. A device as recited in claim 12 wherein said linear track is a first linear track and said guiding means is formed with a second linear track aligned substantially parallel to said axis and formed with a distal end, and wherein said locking cutout is positioned at said distal end of said second linear track with said arm being positioned to deflect said plug from said first linear track to said second linear track and into said locking cutout during distal advancement of said needle guard relative to the needle.

14. A device as recited in claim 12 wherein said plug extends radially from said needle guard.

15. A device as recited in claim 12 wherein said needle guard is formed with a tab and said base member is formed with a slot for interaction with said tab when said plug is located in said locking cutout to prevent rotation of said needle guard relative to said base member.

16. A device as recited in claim 10 wherein said cylindrical needle and said base member are cylindrical shaped.

17. A device for protecting the needle of a syringe, said device comprising:

a hollow cylindrical needle guard defining an axis and formed with a plug extending radially therefrom;

a base member disposed on said needle guard for reciprocal axial movement relative thereto, said base member formed with a locking cutout, a linear track substantially aligned with said axis and a deflectable arm positioned in said linear track and aligned to allow said plug to travel within said linear track from an initial location in said linear track and past said arm during proximal movement of said needle guard relative to the needle without relative rotation therebetween and to direct said plug during distal advancement of said needle guard relative to the needle into said locking cutout to lock said needle guard in a position to cover and protect the needle; and a biasing means disposed between said needle guard and said base member to urge said needle guard and said base member in opposite axial directions.

18. A device as recited in claim 17 wherein said biasing means is a spring.

19. A device as recited in claim 17 wherein said linear track is a first linear track and said base member is formed with a second linear track aligned substantially parallel to said axis and formed with a distal end, and wherein said locking cutout is positioned at said distal end of said second linear track, said arm being positioned to deflect said plug from said first linear track to said second linear track and into said locking cutout during distal advancement of said needle guard relative to the needle.

20. A device as recited in claim 17 wherein one of said base member and said needle guard is formed with a tab and the other is formed with a slot for interaction with said tab when said plug is located in said locking cutout to prevent rotation of said needle guard relative to said base member.

* * * * *

UNITED STATES PATENT AND TRADEMARK OFFICE
CERTIFICATE OF CORRECTION

PATENT NO. : 6,884,237 B2
DATED : April 26, 2005
INVENTOR(S) : Hooman A. Asbaghi It is certified that error appears in the above-identified patent and that said Letters Patent is hereby corrected as shown below:

Column 1,
Line 55, delete "arid" insert -- and --

Signed and Sealed this

Fifth Day of July, 2005

JON W. DUDAS
*Director of the United States Patent and Trademark Office*